United States Patent [19]
Goodall et al.

[11] Patent Number: 5,426,687
[45] Date of Patent: Jun. 20, 1995

[54] LASER TARGETING DEVICE FOR USE WITH IMAGE INTENSIFIERS IN SURGERY

[75] Inventors: John D. Goodall, West Acton, United Kingdom; David E. Young, Watlington, England

[73] Assignee: Innovative Care Ltd., Abingdon, England

[21] Appl. No.: 104,790

[22] Filed: Aug. 10, 1993

Related U.S. Application Data

[63] Continuation-in-part of Ser. No. 909,770, Jul. 7, 1992, abandoned.

[51] Int. Cl.$^6$ .............................................. A61B 6/08
[52] U.S. Cl. ...................................... 378/206; 378/210
[58] Field of Search ................................ 378/206, 205

[56] References Cited

U.S. PATENT DOCUMENTS

| | | | |
|---|---|---|---|
| 5,031,203 | 7/1991 | Trecha | 378/205 |
| 5,283,808 | 2/1994 | Cramer et al. | 378/206 |

OTHER PUBLICATIONS

Smith and Nephew, Memphis, Tenn., 2 catalog pages, date unknown.
Oec-Diasonics, Salt Lake City, Utah, entitled "Laser Aiming Device", 2 pages, date unknown.
Siemens disclosing the "SIREMOBIL 4 Mobile Image Intensifier", date unknown.

*Primary Examiner*—Craig E. Church
*Attorney, Agent, or Firm*—Tilton Fallon Lungmus

[57] ABSTRACT

A laser targeting device for use during surgical procedures provides means for the precise co-axial alignment of a narrow laser beam with an x-ray beam. The device has a case which contains a reflecting mirror mounted at 45° on a low mass assembly. The mirror lies directly in front of a radio-opaque cruciform target. The case is adjustably mounted so that the image of the crosshair target may be accurately centered on the target head. A calibration aid is used to pinpoint the emanation point of the x-ray beam from the source cone of the image intensifier. The angle at which the laser beam strikes the mirror may be varied in two planes. When the crosshair image is centered and the laser beam is directed onto the emanation point the two beams are rendered precisely co-axial. Accurate drilling along the laser beam path without further recourse to x-ray screening is more accurate and eliminates direct exposure of the surgeon to irradiation during orthopedic procedures. A series of special drapes is provided for the device.

6 Claims, 9 Drawing Sheets

LASER TARGETING DEVICE FOR USE WITH IMAGE INTENSIFIERS IN SURGERY

This application is a continuation-in-part of patent application Ser. No. 909,770, filed Jul. 7, 1992, now abandoned.

FIELD OF THE INVENTION

This invention relates to a device for achieving precise co-axial alignment of a narrow laser light beam to a beam of x-rays generated within an image intensifier system. This is achieved without significant degradation of a useful image captured by the system. X-ray image intensifier systems are used by surgeons to locate the positions of radio-opaque artefacts in relation to nearby anatomical or implanted structures in order that they may check, place, augment, fix or remove them.

BACKGROUND TO THE PRESENT INVENTION

Conventional image intensifier systems in clinical use typically comprise the major elements of an x-ray source and a target both supported on a rigid and relatively massive structure that maintains them substantially at 180 degrees to one another. The x-ray source and target are spaced apart by sufficient distance to allow part or all of the patient to be interposed between them. The support is generally referred to as a 'C' arm. The system also includes a monitor screen that displays the image of the body part lying in the x-ray beam.

X-rays and the machines that generate them are hazardous, not only to patients but also to those working with or near them and it is well established that cumulative doses can cause cancer, cataracts and gonadal damage. Operating theatre and radiographic department staff at risk wear lead aprons to protect them from exposure but in some procedures, especially in the field of orthopaedics, the surgeon in particular may have to take a calculated risk and knowingly expose himself to x-radiation.

This practice has increased in recent years with the introduction of reliable intramedullary devices for the fixation of fractures of long bones. Although these devices have led to substantial improvements in fracture management, the techniques for their satisfactory implantation are somewhat demanding.

For example, one device that is increasingly widely used in femoral and tibial fractures is the Grosse-Kempf intramedullary nail. This is a metal tubular structure, with a single slit down its long axis. The diameter of the nail is such that it may be accommodated within the intramedullary canal of the bone. Under general anaesthesia the nail is introduced into the surgically exposed upper end of the proximal bone fragment. The nail is then driven carefully down its length. The fracture is reduced by manipulation of the distal fragment using an image intensifier to ensure that the fragments are correctly aligned. The nail is then driven down into the distal fracture fragment. In order to increase the rigidity of the fixation, transverse locking screws are used at each end of the nail which has holes to accommodate them. Because the nail is a tubular structure the term 'nail hole' in this context really means a front hole and a back hole in the tube. Fixation of the end of the implant at the proximal end, close to the entry site, involves the use of a jig to locate the hole on each side of the nail. This is relatively straightforward because the bone is exposed. However, the holes at the distal end of the nail lie within a part of the bone that is not exposed and can only be located by using x-rays, in particular an image intensifier. It is important to note that the positions of the lower or distal holes cannot be found by direct measurement with reference to the proximal jig. This is because the nail has inherent axial and rotational flexibility; it is not a straight rigid structure and will often twist during insertion.

Although Kempf et al (1985; Closed locked intramedullary nailing (J. Bone Joint Surg. 67A, 709) have described a targeting device which is mounted on the image intensifier, this is difficult to master and the majority of surgeons prefers to use a freehand technique. With this method, in the first stage, the image intensifier is moved to the general area of the limb where the selected nail hole is believed to lie and is then switched on. The 'C' arm and the limb, if necessary, are then manoeuvred until the nail hole is located. This is evident when its image appears upon the monitor screen. Correct alignment is achieved when images of both the front hole and the back hole appear as concentric circles in the middle of the monitor screen.

With the drill held obliquely, the surgeon moves the drill bit over the soil tissue on the surface of the limb to where he estimates the point of entry will be. The x-ray beam is then switched on briefly, during which time at least the surgeon's hand and forearm are exposed to the 'live' radiation. Without moving the drill bit, the surgeon now refers to the monitor screen in order to check the position of the drill bit image relative to the concentric images of the nail hole. If his first guess at the entry point was correct he may choose to mark the limb. This is often done by making a small cruciform stab incision through the skin, sometimes extending down to the periosteum. More often than not the surgeon will need to make at least one and maybe several further screenings in order to position the drill bit accurately, on the soft tissue, over the bone to be drilled. Each screening represents an exposure for the surgeon since it is generally accepted that significant radiation is delivered to objects within 80 cms radially from the axis of an x-ray beam.

Whether he chooses to mark the proposed entry point or not, the surgeon must now make another educated guess regarding how to position the drill in order to make his entry into the bone and engage the nail hole cleanly. This is done by visual reference to the source cone and the target of the inactive image intensifier, the aim being to align the drill accurately with the beam axis which is, of course, invisible.

As will by now be apparent, this entire procedure is difficult, even for the experienced surgeon. It is common for the nail hole to be missed during the first attempt at drilling and this generally necessitates repositioning the drill bit with the x-ray beam on, as before. In addition a drilling 'miss' almost invariably involves some damage to bone.

One of us (J. G.) has collected data which suggests that in the U.S.A. the average x-ray exposure time for a surgeon during an intramedullary nailing procedure probably exceeds 3 minutes whereas in the United Kingdom the exposure time is nearer to 7 minutes.

At this stage we do not have sufficient data to postulate reasons for the difference but it is disturbing that these timings are occurring on recent machines with stored image facilities so that exposure times are already shortened in comparison to those which would occur if images could not be stored. What is clear is that, if intramedullary nailing remains popular during the next few decades, a surgeon aged thirty when he takes up the technique and carrying out one procedure per week, could receive a cumulative dose of x-rays equivalent to over 150 hours continuous exposure. This is a frightening prospect and one that should concern all surgeons carrying out these procedures.

The orthopaedic establishment is now aware of the dangers. In an editorial article in the Journal of Bone and Joint Surgery in May 1992, Hynes et al, wrote "The recent upward revision of risk estimates should serve as a timely warning to all occupationally-exposed radiation workers, including orthopaedic surgeons, that there continues to be uncertainty in predicting the effects of low dose radiation, and that it is wise to act on the basis that there is no safe dose of radiation." (Ionising radiation and the orthopaedic surgeon. J. Bone Joint Surg [Br] 1992: 74B: 332-4).

Accordingly, we have invented and developed a device that substantially reduces this risk and which is in line with current attitudes and accepted techniques for preserving the personal safety of those working in the operating room, those operating x-ray apparatus and patients exposed to this form of ionising radiation. The instant invention is also in accordance with the 'Alan (As Low As Reasonably Achievable) Principle'- (Euratom 1980).

A single low power laser beam, suitably aligned and positioned so as to be co-axial with the x-ray beam of an image intensifier system, would also lie along the axis of an intended drill hole in a bone, once the limb had been correctly positioned. This would enable accurate alignment of the drill to the axis of the x-ray beam to be achieved by reference to the laser light and without additional reference to x-ray screening. This would significantly eliminate direct exposure of the surgeon. Until now, means for achieving this have presented significant mass in the beam path with consequent degradation of the image. This is not a great problem with patients who have good quality bone because they generally yield clear images, however, in older and osteoporotic patients the images are often rather unclear and any significant degradation is unacceptable.

THE PRIOR ART

We are aware of a laser targeting device for use with an image intensifier. This is made and supplied by Messrs Siemens of Erlangen, Germany. This device has two laser sources mounted near the x-ray source, each producing a flat laser beam, the second at right angles to the first. Both beams are directed towards the target in the same general direction as the x-ray beam. The laser beams produce a cruciform image on the image intensifier target (or on a limb surface if one is interposed) at the point of impingement of the x-ray beam. The laser system does not produce any image on the monitor screen. However, because the laser beams emanate from the source end of the image intensifier system, the use of this system appears to us to be mainly restricted to use with targeting for drilling into the distal femur. This is because the femur can be drilled from either side whereas the tibia is drilled from the medial side in order to avoid the fibula. A further limitation is that the device is only supplied with certain current models of this manufacturer's image intensifier machines and this will preclude its use by the majority of surgeons. Furthermore the device is expensive and may be beyond the budgets of many hospitals. Finally, in many procedures, the 'C' arm image intensifier system is so positioned that the source cone underruns the edge of the operating table in which circumstances the laser beams cannot be seen.

We are also aware of several mechanical jigging devices designed to be set up on the limb, in the image intensifier system beam, with the intention of providing good alignment of the drill bit with the nail holes. Most surgeons find these awkward to use and that they restrict the field of view.

Finally we are aware of a drill made by Messrs AO Synthes of Bochum, Germany in which all the parts are plastic and only the drill bit is fully radio-opaque. This device is, however, intended to be held directly in the live X-ray beam (there can be no other reason for its being made somewhat radio-lucent) and this would seem to exacerbate the problem of exposure of the surgeon. In addition the presence of a relatively large mass of plastic in the X-ray beam has been observed to lead to loss of clarity in the images of the holes and other structures.

OUTLINE OF THE PRESENT INVENTION

According to one important aspect of the present invention, there is provided a laser source suitably housed and which generates a narrow beam. The laser housing is attached to a case which is provided with means for mutual adjustment between it and clamping means which are provided to co-operate with the target head of image intensifier machines in common use, securing it in place.

According to a second important aspect of the present invention, there is provided, within the housing, laser beam-directing apparatus.

According to a third aspect of the present invention, there is provided within the case a reflecting mirror borne upon a mount of minimal mass and held in a fixed geometric relationship to the laser source.

According to a fourth important aspect of the present invention, there is provided target means for producing a visual reference on an x-ray image intensifier monitor screen. The adjustment means of the first aspect enables alignment of the image of target means to the effective centre of the target head of the image intensifier.

According to a fifth aspect of the present invention there is provided a calibration aid which provides radio-opaque means and marking means for locating and marking the point on an image intensifier system source cone from which the x-ray beam emanates.

According to a sixth aspect of the present invention there is provided a draping system so that the instant device may be safely taken into a sterile field.

DESCRIPTION OF THE DRAWINGS

In order that the present invention may be more readily understood, reference will now be made to the accompanying drawings of a best mode, most preferred embodiment in which.

Figure 1:
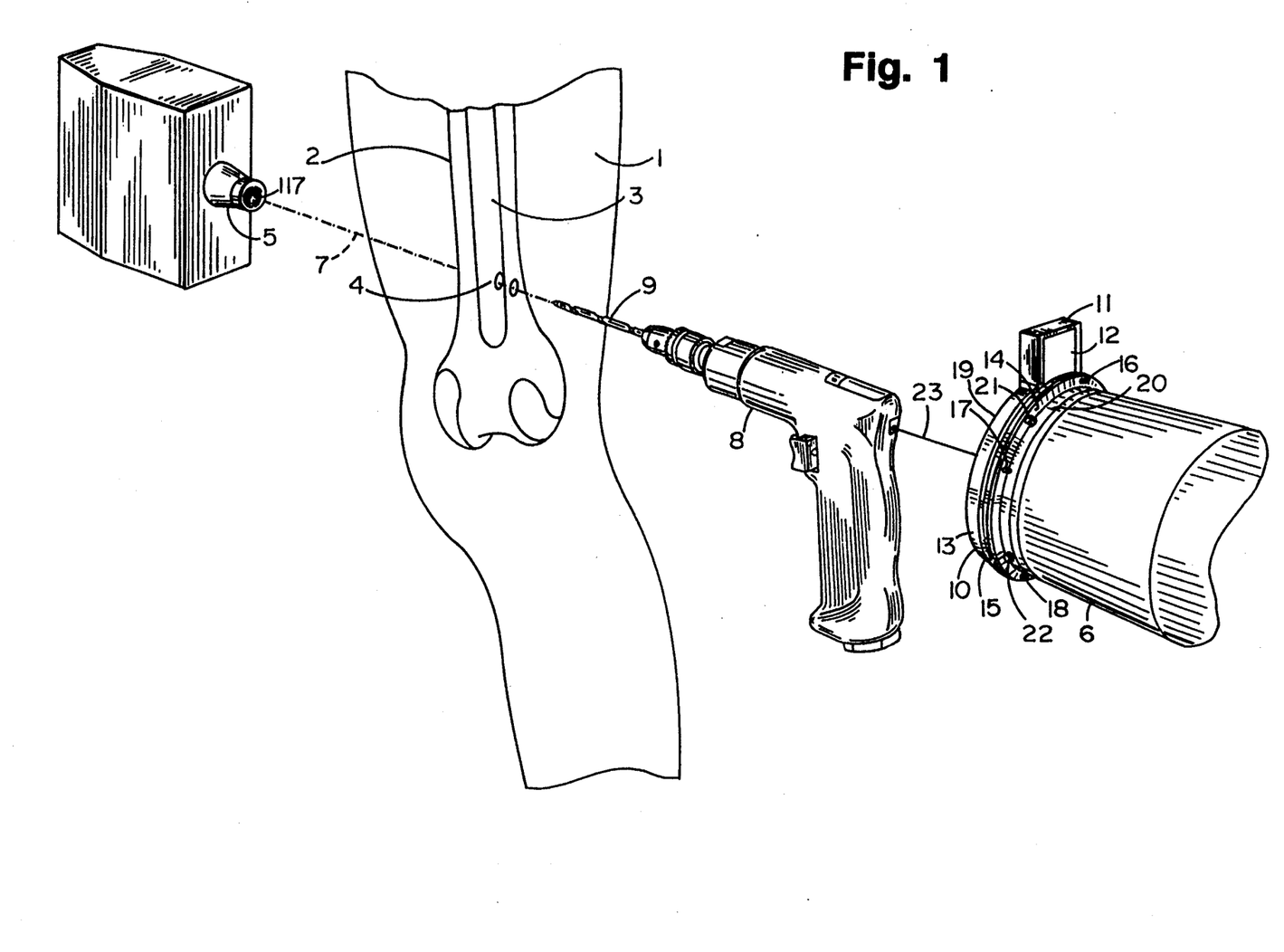
FIG. 1, is a diagrammatic side-view representation, not to scale, of the principles of use of a laser targeting device, according to the present invention, in conjunction with an image intensifier, for drill alignment preparatory to drilling holes for distal transverse locking screws during an intramedullary nailing procedure.

In FIG. 1, a mammalian lower limb 1, is shown in diagrammatic cross section in which the femur 2, has an intramedullary nail 3, driven down it. A hole 4, passes transversely through intramedullary nail 3 and is adapted to receive a transverse locking screw (not shown). An image intensifier system source cone 5 and target head 6, are aligned with nail hole 4. The axis of an x-ray beam used to achieve this alignment is shown by broken line 7. It should be noted that some skilled in the art will prefer the terms 'receiver' or 'receiver head' to the term 'target head'. A surgical drill 8, is fitted with a drill bit 9, and is precisely aligned with nail hole 4, by reference to laser beam 23.

According to a first important aspect of the present invention, a laser targeting device with the general designation 10, has a housing 11, which contains a laser source (not shown in this view). Housing 11, has a lid 12 and is attached to a case 13. Case 13, is closed off above by upper plate 14 and these four elements 11–14, form assembly 15. In this embodiment, upper plate 14, is provided with three sets of screw locking means 16, 17 and 18, which are adapted to secure it between collar 19 and clamping frame 20. Clamping frame 20, is provided with 3 sets of clamp means of which two, 21 and 22, may be seen in FIG. 1. By means of these clamps, which in this embodiment are adapted by the provision of screw means, clamping frame 20, secures assembly 15 and in particular upper plate 14, flush against the front of image intensifier target head 6. It is to be understood that because the design of target heads of image intensifiers varies considerably, clamping frame 20, will or may be custom made for each machine variant.

A narrow laser beam is caused to be emitted from the laser source. This beam is represented by solid line 23 and is directed by means according to the present invention and described hereunder with reference to FIGS. 3, so as to be precisely co-axial with the x-ray beam axis represented by broken line 7. It will now be appreciated that surgical drill 8 and drill bit 9 are precisely aligned with nail hole 4, by reference to laser beam 23.

Figure 2:
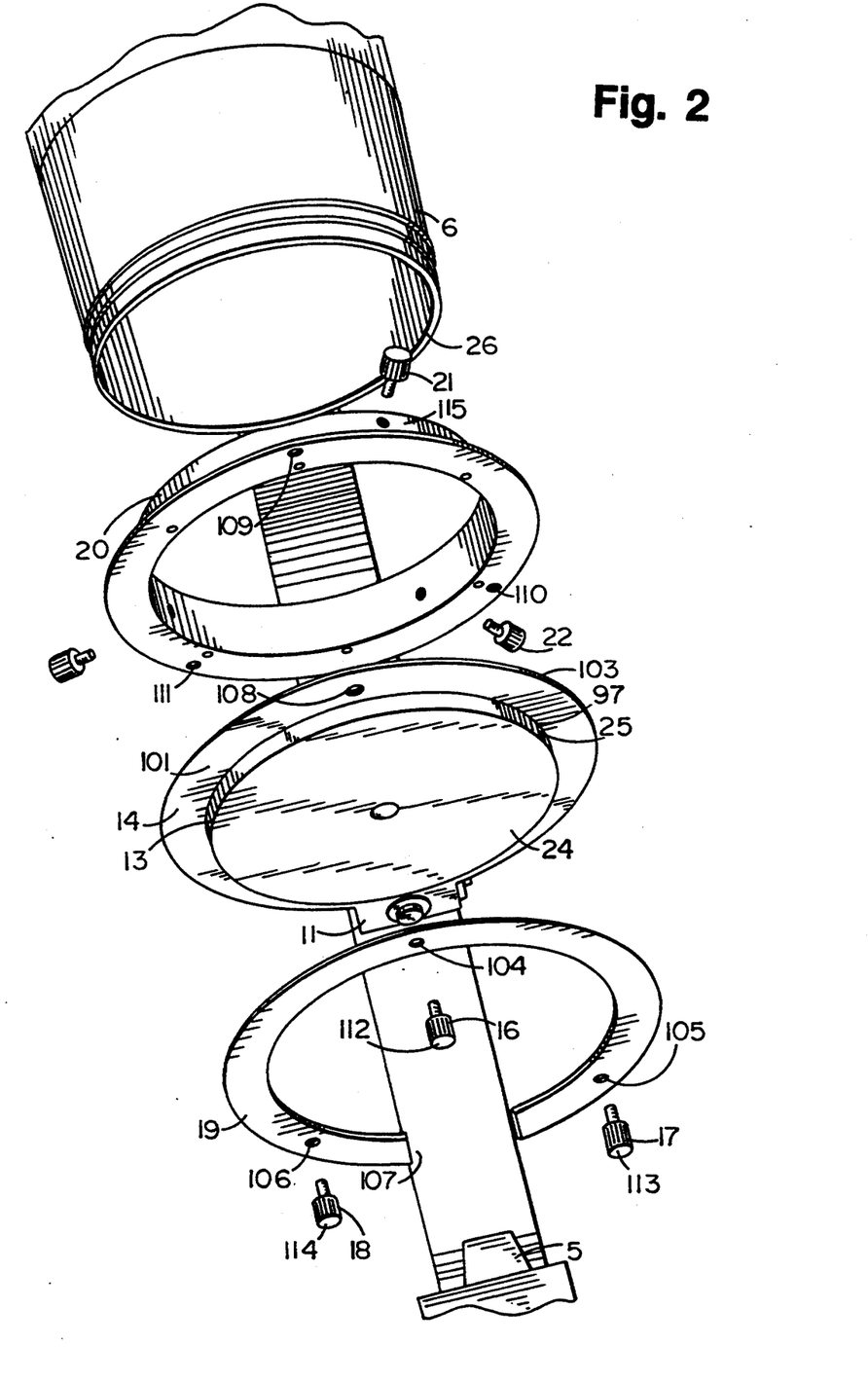
FIG. 2, is an exploded, perspective view of the larger components comprised in a major assembly which forms part of a laser targeting device, according to the present invention.

FIG. 2, is an exploded, perspective view of the assembly 15, of FIG. 1, seen from below. This view shows the relationships between the major structural elements of the instant device and also indicates its typical position with respect to a 'C' arm image intensifier system during use. Components are made from suitable non ferrous engineering materials such as aluminium alloy. Floor 24, constitutes the lower bounding surface of case 13 and upper plate 14, constitutes the upper bounding surface of case 13. Since wall 25, of case 13, is of constant dimension throughout what is effectively its circumference, the upper and lower bounding surfaces must necessarily be disposed in a substantially parallel manner. Both floor 24, of case 13 and upper plate 14, are of a minimum thickness consistent with reasonable resistance to denting during day to day use. Consequently these elements are substantially radiolucent and image intensifiers with automatic correction for image density have shown voltage rises only in single figure percentages. Although only part of upper plate 14, is shown in FIG. 2, it should be clear that it is adapted, by virtue of flatness, to lie flush against the working area 26, of target head 6 and further that it is adapted to be retained in place by co-operation with the elements of clamping frame 20, in conjunction with screw locking means 16–18 and collar 19.

Figure 3:
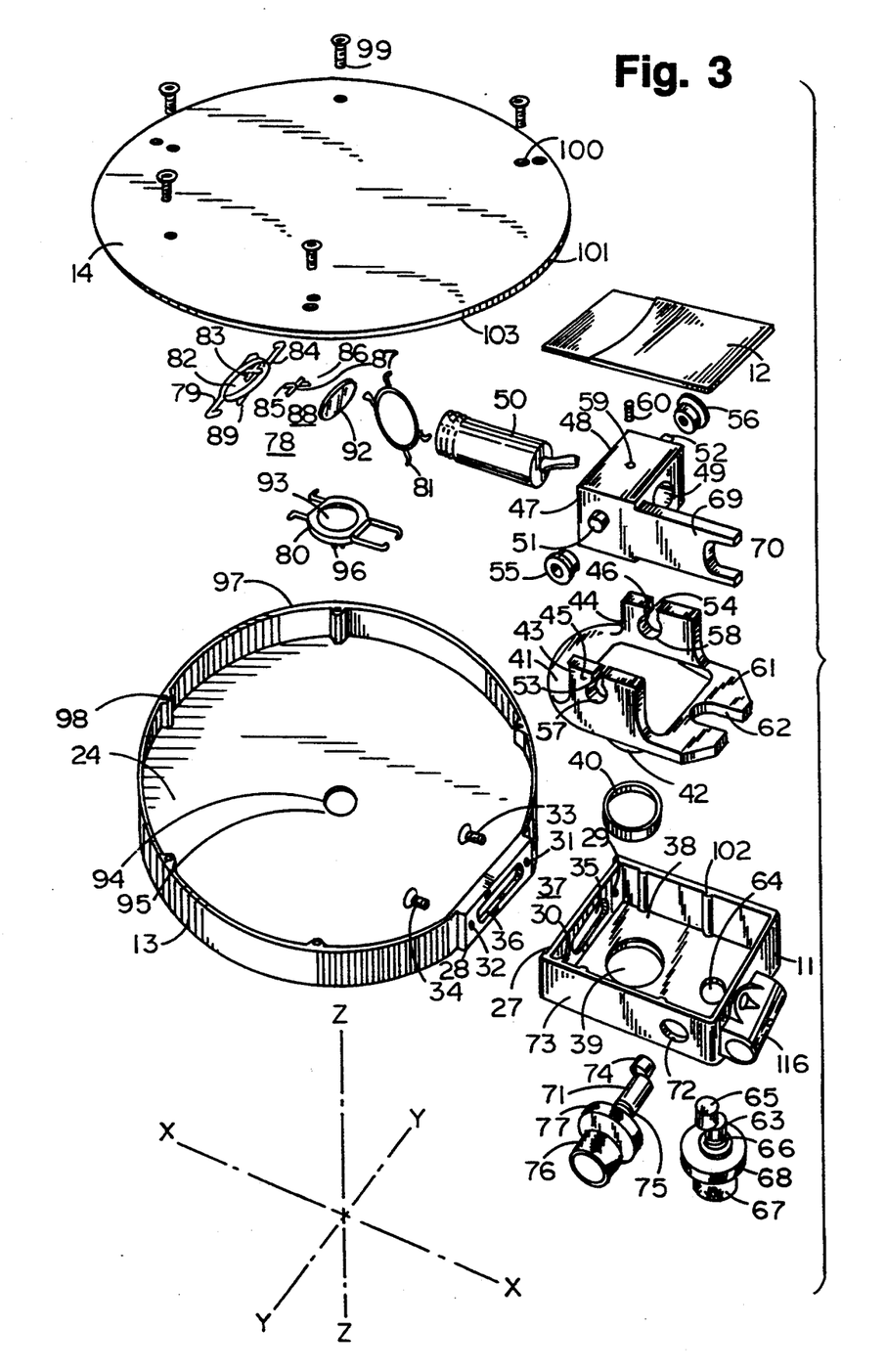
FIG. 3, is an exploded perspective view of the principal functional parts of laser beam directing means, mirror mount assembly and target means according to the present invention.

FIG. 3, shows housing 11 and case 13, mutually adapted by the provision of corresponding 'female' and 'male' profiles 27 and 28, respectively, constituting receival means. Holes 29 and 30, in housing 11, are adapted by the provision of thread means (not seen) and match holes 31 and 32, in case 13, which are minimal clearance holes for screw means 33 and 34, constituting together mounting means for housing 11, on case 13. These mounting and receival means are provided to ensure that housing 11 and case 13, fit together precisely and are retained in a fixed geometrical and structural relationship such that no part of housing 11, covers any part of the working area of image intensifier target head 6. It will be appreciated by those skilled in the art that elements 11 and 13, could be manufactured in one piece. Housing 11 and case 13, also have similarly sized and shaped concentric holes 35 and 36, respectively, which together, in the assembled condition constitute an aperture 37, through which the laser beam passes.

According to a second important aspect of the present invention, it may be seen in FIG. 3, that in the floor 38, of housing 11, is machined a circular recess 39, which receives circular bearing bush 40. Bearing bush 40, is constructed in conventional bearing materials. Turntable 41, is conveniently formed in aluminium alloy and is adapted by means of circular bearing extension 42, to fit firmly into bearing bush 40. Turntable 41, has substantially identical lateral upward extensions 43 and 44, each of which is provided with banjo shaped keyhole slots 45 and 46, respectively.

Laser mount 47, is conveniently formed in aluminium alloy and has a main portion 48, which is generally a parallelepiped with a cylindrical hole 49, disposed about its long axis. Hole 49, is so sized that it will just accept laser source 50, which is cylindrical, as a sliding push fit. Laser source 50, is a low power Helium/Neon device.

Laser mount 47, is provided with substantially identical lateral cylindrical extensions 51 and 52, which constitute bearings. Bearings 51 & 52, are of such a diameter that they will pass down parallel sided portions 53 and 54, of keyhole slots 45 and 46. Cylindrical bushes 55 and 56, are substantially identical and are so sized that they form a press fit over bearings 51 and 52. They are also a tight press fit into circular portions 57 and 58, respectively, of keyhole slots 45 and 46. This arrangement also secures laser mount 47, to turntable 41, in the appropriate functional position. A small hole 59, in main portion 48, of laser mount 47, is provided with thread means (not shown) and is adapted to receive a grub screw 60, which provides securing means for laser source 50.

Base 61, of turntable 41, is provided with a slot 62, adapted to receive an adjuster 63. Adjuster 63, passes through a hole 64, located in the floor or first side 38, of housing 11, suitably adapted to receive it as a firm push fit. That part of adjuster 63, which engages with slot 62, is adapted to form a cam 65, whilst that part of adjuster 63, which lies outside housing 11, is provided with a threaded portion 66 and a turnwheel 67. A lockwheel 68, is provided with thread means (not shown), adapted to receive threaded portion 66, of adjuster 63.

Starting with turntable 41 in its mid position, operating turnwheel 67, causes turntable 41 and hence laser mount 47, to make a small angular excursion in the x-y plane about the z axis and away from the mid position. This is occasioned by cam 65, operating against slot 62. Further operation of turnwheel 67, causes cam 65, to drive turntable 41 and laser mount 47, assembly back towards the mid position. Continuing to operate turnwheel 67, drives turntable 41 and laser mount 47, away from the mid position and if this is continued the assembly completes the cycle of reciprocal motion and once more returns to the mid position.

Similarly, a backwards extension 69, of laser mount 47, is provided with a slot 70, adapted to receive an adjuster 71. Adjuster 71, passes through a hole 72, located in one wall or second side 73, of housing 11, suitably adapted to receive it as a firm push fit. That part of adjuster 71, which engages with slot 70, is adapted to form a cam 74, whilst that part of adjuster 71, which lies outside housing 11, is provided with a threaded portion 75 and a turnwheel 76. A lockwheel 77 is provided with thread means (not shown) and is adapted to receive threaded portion 75, of adjuster 71.

Operating turnwheel 76, causes laser mount 47, to make small upwards and downwards angular excursions in the x-z plane about the y axis away from its mid position. This is occasioned by cam 74, operating against slot 70, to produce reciprocal motion.

Cam 74, has sufficient length such that when turntable 41, is caused to move in the horizontal plane, slot 70 may traverse over cam 74, in a reciprocating manner without either disengagement of the working parts or impingement of inappropriate parts.

According to a third aspect of the present invention it may be seen in FIG. 3, that a mirror mount assembly 78, is located centrally within the floor 24, of case 13. Mirror mount assembly 78, comprises a mirror mount 79, a transparent window base 80 and an angled ring support member 81. All three elements of mirror mount assembly 78, are moulded in suitable radiolucent plastics and are low mass components designed to present minimal cross sections to an x-ray beam passing through floor 24, of case 13, normally to it. Elements 79–81, of mirror mount assembly 78, are preferably solvent welded to one another and are so sized and adapted that the angle enclosed between mirror mount 79 and transparent window base 80, is 45°.

According to a fourth important aspect of the present invention there is provided target means for producing a visual reference on an x-ray image intensifier screen. Mirror mount 79, is formed with a recess 82, so shaped and sized as to accommodate the former as a firm press fit. Recess 82, is further adapted by having two straight grooves 83 and 84, formed in it at right angles to one another and are formed to such a depth and width as to constitute press fit mounting means for lead wire strips 85, 86 and 87. Lead is a densely radio-opaque material and together these strips constitute a cruciform target 88. It should be noted that various other radio-opaque materials could be used as alternatives to lead wire for target 88. When assembled, lead wires 85–87, lie minimally under-flush with respect to the floor 89, of recess 82.

When mirror mount 79, is positioned correctly (see below), groove 83, which is formed along part of a diameter, lies precisely in the x-z plane of device 10. Groove 84, on the other hand, is formed along a line offset above the equator of recess 82 and therefore, does not lie on a diameter.

Figure 4:
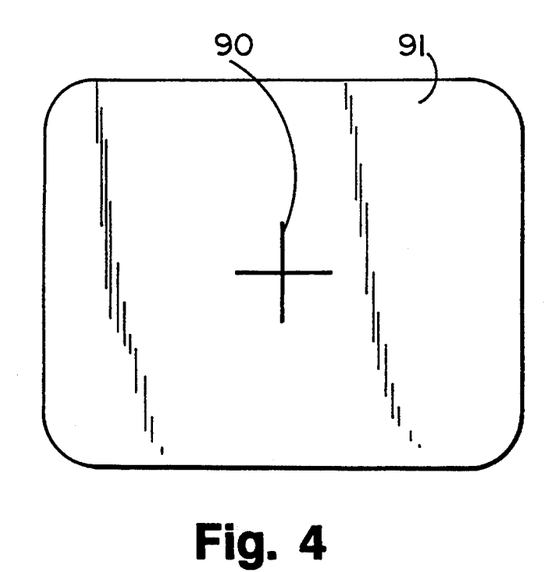
FIG. 4, is a diagrammatic representation of the monitor screen of an image intensifier showing target means according to the present invention.

Groove 83, is longer than groove 84, to the extent that when target 88, is properly located within mirror assembly 78, of the complete device 10 and is exposed to x-rays, the image 90, produced on an image intensifier monitor screen 91, is cruciform in shape with all four arms being apparently of equal length. The effect may be seen by brief reference to FIG. 4.

Returning to FIG. 3, reflecting mirror 92, clips into recess 82 and is secured in place with suitable adhesives over target 88. Reflecting mirror 92, is front silvered to eliminate refractive and duplicative effects that would occur with a back silvered mirror.

Transparent window base 80, is adapted by the provision of a downward extension 93, which matches exactly in depth and plan shape, a corresponding hole 94, in floor 24, of case 13. The length of extension 93, matches the thickness of floor 24, so that when these elements are assembled using suitable adhesives, extension 93, is flush to the outer face (not seen) of floor 24.

Hole 94, has a plurality of locating recesses disposed about its circumference and indicated by way of example at 95, which match a set of lugs, on extension 93, of transparent window base 80 and indicated by way of example at 96. Recesses 95 and lugs 96, are disposed in an angular relationship such that they may only be assembled in one orientation, namely that which will present mirror 92, at 90° to the x-z plane and 45° to the x-y plane of device 10.

When turntable 41 and laser mount 47, are in the respective mid positions of their available movement range, laser source 50, lies exactly along the x-axis and a laser beam emitted from it will strike the centre of reflecting mirror 92 and be deflected through 90° in the x-z plane so that it will pass through transparent window base 80, in the centre of extension 93 and normal to it.

Rim 97, of case 13, is provided with a plurality of mounts indicated by way of example at 98, each of which is provided with thread means (not seen) for receiving countersunk screw means indicated at 99. Upper plate 14, is provided with a plurality of countersunk holes, indicated by way of example at 100, in positions which correspond to the mounts in case 13 and as may be seen by brief reference to FIG. 2, disposed in such a way that when it is secured in place with screw means 99, it provides an overhang or lip 101, extending a constant radial distance beyond rim 97, of case 13.

Returning to FIG. 3, it may be seen that lip 101, also covers part of laser housing 11, which, like case 13, has a plurality of mounts, within its rim, each provided with thread means (not shown) and indicated by way of example at 102. Lid 12, is so shaped and adapted as to close off laser housing 11 and to shut off against the underside (not shown) of circular edge 103, of upper plate 14.

By further reference to FIG. 2, the relationship between the adjustment means of the first aspect of the present invention and the target means of the fourth aspect may now be illustrated. Collar 19, is an incomplete circular structure provided with a series of clearance holes 104–106, disposed at 120 degree intervals and positioned at the mid point of the radial distance between its inner and outer circumferences. Collar 19, including that portion of it which is interrupted, indicated at 107, is so sized that it during assembly of laser targeting device 10, it will clear laser housing 11 and lie flush against the underside of upper plate 14. Holes in a corresponding series, in upper plate 14, of which only one 108, may be seen, are considerably larger. Clamping frame 20, is conveniently, though not necessarily, machined from a single piece of aluminium and also has a corresponding series of holes 109–111, each having a diameter slightly less than that of holes 104–106, in collar 19 but in this case each provided with thread means, conveniently of the type known to those skilled in the art as hank bushes (not seen). Clearance holes 104–106, in collar 19, larger holes in upper plate 14, exemplified by 108 and holes 109–111, with hank bushes, in clamping plate 20, are all adaptations for the receival of screw locking means 16–18. Collar 19, has an inner radius that is somewhat greater than that of the outside of case 13. Holes exemplified by 108, in upper plate 14, have a radius equal to the difference between the inside radius of collar 19 and that of the outside of case 13, added to the diameter of the screw means 16. Interrupted portion 107, of collar 19, clears laser housing 11, by a linear distance slightly greater than the difference between the inner radius of collar 19 and that of case 13. Screw locking means 16–18, pass through holes 104–106 and the series exemplified by 108, respectively and engage hank bushes in holes 109–111 respectively. In order to clamp collar 19, upper plate 14 and clamping plate 20, together, screw locking means 16–18, must be turned down firmly. Ample clamping force is obtained with screw locking means 16–18, by manually turning knobs 112–114.

It is to be clearly understood that clamping ring 20, has a radius which will necessarily vary according to the radius of the x-ray image intensifier receiving head to which the laser targeting device 10, is to be fitted and indeed, in some cases, vertical portion 115, of it may have to be some shape other than a circle or it may need to be an incomplete circle. This may be accommodated without departure from the present invention herein disclosed.

In FIG. 3, it can be seen that an electrical socket 116, is fitted to the rear of laser housing case 11. Wires (not shown) connect the socket to the rear of laser source 50 and are configured as a single overlength coil (not shown) to ensure that they may readily accommodate all adjustment positions, without overstrain or traction developing on the wiring or laser source 50. A simple but robust two wire covered lead with a suitable plug at one end and a socket at the other is used to conduct power from a suitable enclosure used as a remote switch box and housing a 9-volt cell of the general type PP9. Power is switched on and off with a single pole switch in series with the negative pole of the cell and also in series with a low power light emitting diode which acts as a status indicator. A convenient lead length is 2 to 3 meters.

With brief reference to the foregoing drawings FIGS. 1–3, especially FIG. 3, it will now be appreciated that housing 11 and the majority of other components hereinbefore described are adapted and assembled so that reflecting mirror 92, lies directly in the path of a narrow laser beam produced by laser source 50. The purpose of reflecting mirror 92, is to turn the laser beam through 90 degrees, with a few degrees of angular adjustment in each of two planes being provided for by the reciprocating motions of turntable 41, laser mount 47 and their co-operating structures. The laser beam is generated from within housing 11, by laser source 50, which is housed outside the image intensifier target head working area 26. This ensures that the body of the laser source 50, does not form an image which might otherwise interfere with the procedure.

The position of reflecting mirror 92, within mirror mount assembly 78, ensures that the laser beam is directed out through transparent window base 80, into precise co-axial alignment with an X-ray beam emanating from an image intensifier system source cone 5, subject to relevant adjustments having been made. The adjustments will be shortly hereinafter be described.

Materials are selected for radiolucency, so far as is possible and their mass is also minimised, commensurate with adequate mechanical strength, to ensure that any degradation of the image is barely perceptible.

The exception is the lead wire cruciform target 88, the purposes of which include providing technicians and surgeons using the device with the certainty that laser targeting device 10, is properly centered on image intensifier target head 6 and with a precise point of reference to the functional centre of the monitor screen 91—see below—so that they may know their exact position in relation to the patient. Care has also been taken to ensure that nothing that will substantially degrade the laser or mirror performance is allowed to enter the device.

Accordingly, downward extension 93 of transparent window plate 80, prevents ingress by dust and other contaminants and upper plate 14, in co-operation with lid 12 prevents ingress of contaminants from the other side of the device.

Locating and Marking the Emanation Point of the X-ray Beam from the Source Cone of the Image Intensifier This is best done before the laser targeting device 10, is attached to target head 6.

Many image intensifiers have a target head, which can be rotated mechanically around its central axis. This produces angular rotation in the image equal to the angular rotation of the target head. Other machines employ electronic means to rotate the image.

In either case, before using the laser targeting device 10, according to the present invention, it is essential to establish the precise centre of emanation of the X-ray beam from the source cone 5. It might be thought that this will always be in the centre of the source cone but experience has shown that this is often not the case, probably because many image intensifiers are mobile and the source cone is often struck against door frames and other solid objects as the machine is wheeled in and out of the operating room. This mechanical damage can displace or distort the conical cover over the actual source beneath it. Having said this, it will be found, very frequently, that the emanation point is central to the source cone.

Figure 5:
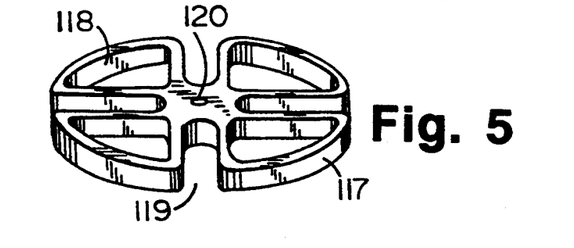
FIG. 5, is a perspective view of the underside of a calibration aid, according to the present invention, used for locating the emanation point of an x-ray beam from a source cone of an x-ray image intensifier.

According to a fifth aspect of the present invention, there is shown in FIG. 5, an underplan view of a calibration aid 117, conveniently made as an injection moulding. Calibration aid 117, is substantially circular, having the general plan shape of a shamrock flower with four symmetrical recessed portions, indicated by way of example at 118 and having slots between them, indicated by way of example at 119. A small steel ball 120, conveniently about 0.5 mm in diameter, is fitted to the centre of the moulding.

Calibration aid 117, is used by pressing a small amount of modelling clay or other suitable, non-permanent, tacky material into the recesses and then sticking it gently on source cone 5. It may be seen in position by brief reference to FIG. 1. After observing all normal safety precautions, the image intensifier machine is switched on for a moment—this is called 'screening'. After screening, either a photographic print is obtained or the stored image is displayed on the monitor. The image of the small steel ball 120, will be in the effective centre of the image if the maximum flux density of the beam was emitted from directly beneath it. In order to be quite certain that the image is in the centre of the screen, the latter is rotated and the screening is repeated.

If the ball image is off-centre it will appear to jump to a new position when the second screening is played back or printed out. It is possible to establish very quickly where the maximum flux emanation point on source cone 5, is with any machine maintained to a reasonable standard, simply by repeating the screening once or twice more, repositioning calibration aid 117, between each event.

Even more accuracy can be obtained by rotating target head 6, whilst continuously screening in real time since this will show very clearly any precession of the image on the screen.

With calibration aid 117, still in place, a permanent marker is used to mark the emanation point on source cone 5. This is conveniently done by inserting the point of the marker into the slots exemplified by 119, between each of the recessed portions, exemplified by 118, in turn, to make a series of radial marks. Calibration aid 117, is then removed leaving four straight radial marks disposed at right angles about the emanation point.

Calibration aid 117, is normally removed once the emanation point on source cone 5, has been established.

Alignment of The Laser Targeting Device to the Target Head of the Image Intensifier Once the emanation point of the X-ray beam from source cone 5, has been determined, clamping frame 20 and hence all of laser targeting device 10, is secured to and against the image intensifier head 6, using three sets of clamp means, disposed 120 degrees apart.

We have found that there is considerable variety in the shapes of image intensifier heads. Some are cylindrical, some are tapered, some have annular grooves or rings and the range of diameters is considerable. For these reasons we use clamping frames constructed specifically for each individual machine. We prefer a three point fixing because it confers stability. Mounting and demounting is generally straightforward. It is important that upper plate 14, is positioned flush against the underside of target head 6.

The aim of this procedure is to align the cruciform radio-opaque target 88, on mirror mount 79, with the effective centre of image intensifier target head 6. The method is a 'screen and check' exercise that is in some respects similar to that used for finding the emanation point of the x-ray beam from source cone 5.

The normal safety procedures are then observed and the image intensifier system is screened. When the photograph or monitor is viewed, the image 90, of target 88, will be seen near the centre of the screen—see FIG. 4.

As noted above, image intensifiers have a target head 6, which can be rotated either mechanically or electronically around the central axis. This produces angular rotation in the image equal to the angular rotation of the target head. Therefore, in order to be quite certain that the image is in the centre of the screen, the latter is rotated and the screening is repeated.

If cruciform target 88, is off-centre, its image will precess to a new position when the second screening is played back or printed out. A small number of repeat screenings in various positions will quickly establish the true position of the target over the effective centre of the target head on any machine maintained to a reasonable standard simply by repositioning between each event.

This is done by gently slackening screw means 16–18, which action will allow assembly 15, to be moved whilst still being retained by collar 19. Screw means 16–18, are then re-tightened, clamping assembly 15, firmly in a new position. Re-screening is then carried out and if necessary, the adjustment procedure is repeated.

Even more accuracy can be obtained by rotating target head 6, whilst continuously screening in real time since this will show very clearly any precession of the crosshair image on the screen.

The arrangement of the adaptations comprising holes 104–106, in collar 19, screw means 16–18, larger clearance holes in upper plate 14, exemplified by 108 and holes 109–111, with hank bushes in clamping frame 20, allows assembly 15, in this embodiment to be moved a total of 10 mm (+5 mm or −5 mm) along both its x-axis and its y-axis. This range of movement is adequate to compensate for any reasonable damage which may have occurred to the casing of a target head causing minor malalignment of the head and its case. It is also sufficient to compensate for any variation in the way clamp means including 21 and 22, are fitted since necessarily there must be some clearance for clamping ring 20, about target head 6.

Angular Adjustment of The Laser Beam—Fine Alignment of the Laser Beam and X-ray Beam Lockwheels 68 and 77, are slackened slightly and laser source 50, is switched on from the remote switch box. This causes a red laser light spot to appear on or very near source cone 5. Turnwheels 67 and 76, are now manipulated to bring red laser light spot 121, directly onto the centre of the radial markings made on source cone 5. Lockwheels 68 and 77, are then re-tightened and the laser is switched off until needed.

The combination of the image intensifier and a laser targeting device, according to the present invention, is now ready for use and may be draped for inclusion in the sterile field.

Difficulties Encountered in Setting Up the Laser Targeting Device

During the development of this device we have encountered several problems and odd situations during setting up. Sometimes we found that the emanation point of the x-ray source could not be determined because it was too diffuse or too far off-centre. In such situations the image intensifier has always been found subsequently to be faulty and we believe that under such circumstances it is unwise to rely on the adjustment facilities on the instant laser targeting device. Instead the image intensifier should be serviced in order to remedy the problem.

Using The Laser Targeting Device

Figure 6:
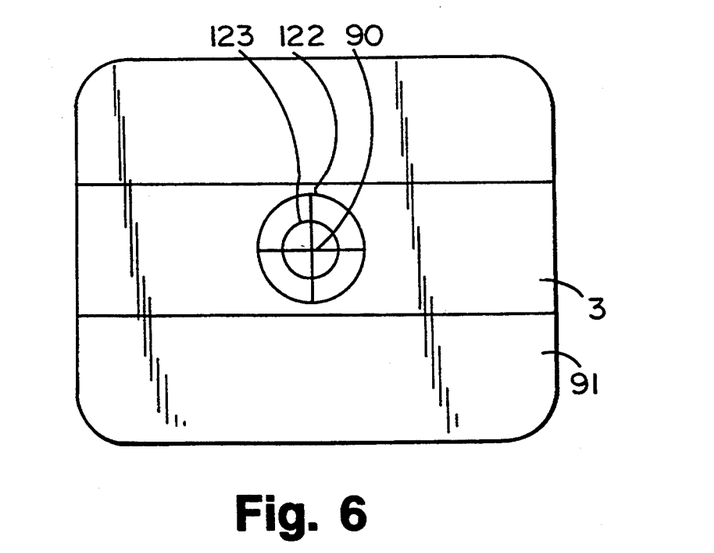
FIG. 6, is a diagrammatic representation of the monitor screen of an x-ray image intensifier showing target means according to the present invention aligned with front and rear distal locking holes of an intramedullary nail.

Turning now to FIG. 6, there is shown a diagrammatic representation of an image intensifier monitor screen 91 and the image 90, of cruciform radio-opaque target 88, superimposed on circular images 122 and 123, formed by the holes in the front and rear surfaces respectively, of an intramedullary nail 3.

It will be evident that X-rays will pass through reflecting mirror 92, as soon as the beam is switched on. Reflecting mirror 92, is substantially radiolucent but on some machines it does produce a very faint image which may be noticed on the image intensifier monitor. However, this effect is insignificant in comparison with the image 90, produced by target 88, which lies immediately behind reflecting mirror 92 (when considered from the point of view of the incident x-ray beam).

It will now be appreciated that target 88, has two functions. Firstly, it enables laser targeting device 10, to be aligned to the image intensifier x-ray apparatus, in particular to the target or receiver head 6. Secondly, it provides an absolute point of reference both to the effective centre of the working area 26, of target head 6 as well as to the distal locking holes in an intramedullary nail. Furthermore, the image 90, of target 88, is small enough to lie more or less within the concentric images 122 and 123, of the aligned holes; indeed its presence is of considerable help in achieving that alignment.

Figure 7:
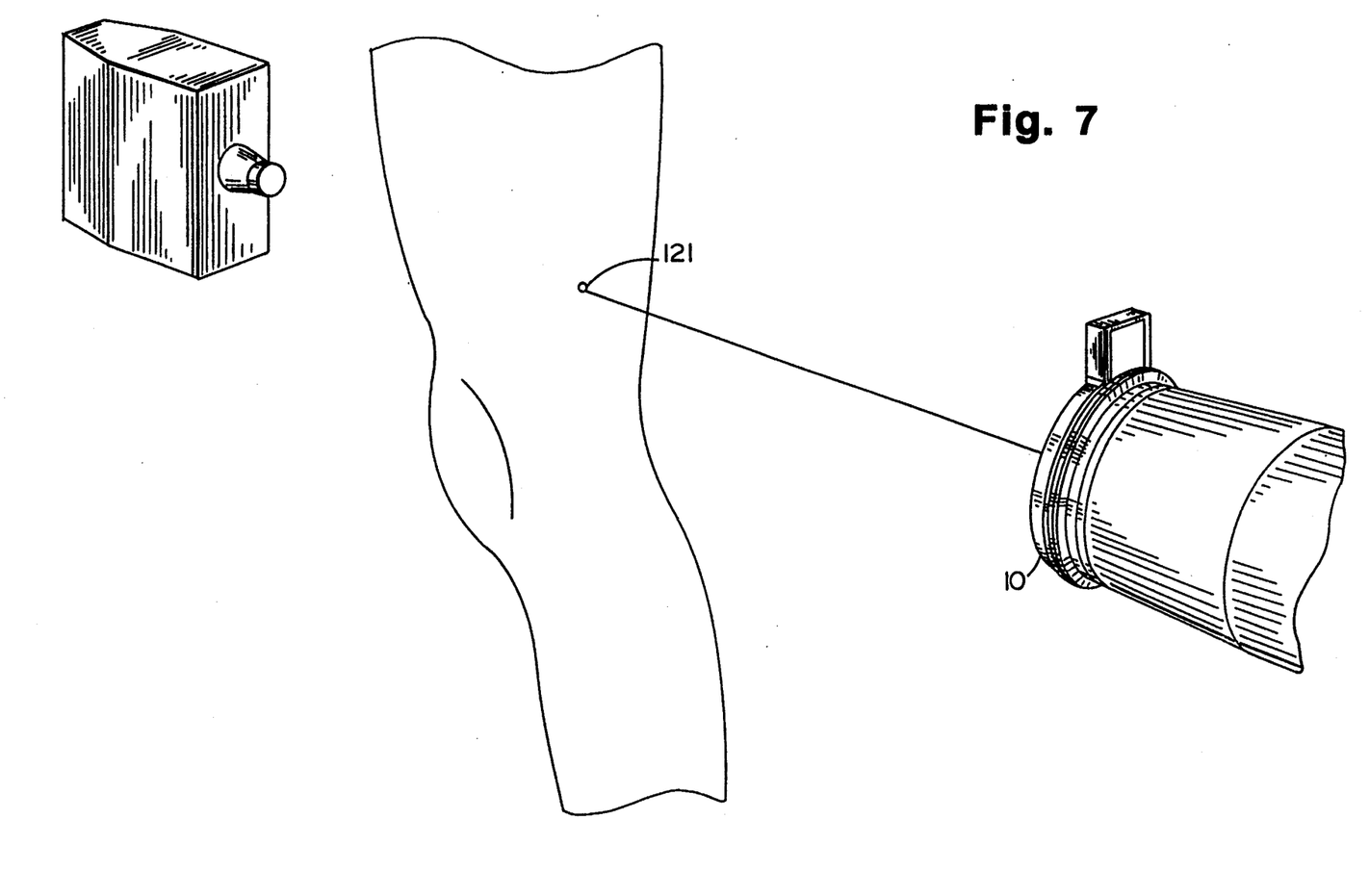
FIG. 7, is a perspective diagrammatic view of a low power laser beam incident upon a limb interposed between the source and target of an image intensifier to which a laser targeting device, according to the present invention, is attached and aligned.

In FIG. 7, the application of a laser targeting device 10, in conjunction with an image intensifier target head 6, during an intramedullary nailing procedure is shown in diagrammatic form. The procedure is carried out in the usual way, up to and including the point where the hole alignment is achieved, as may be seen by brief reference to FIG. 6. Once alignment is achieved, the image intensifier system x-ray beam is switched off and laser source 50, is switched on. A red laser light spot 121, will appear on the limb 1, directly over the front and rear nail holes (not seen in this figure—refer to FIG. 1 ) and indicating the correct axis for drilling. This position may now be marked, if the surgeon wishes. Marking is usually done either with a sterile skin marker or more commonly by means of a cruciform incision with a scalpel.

Figure 8:
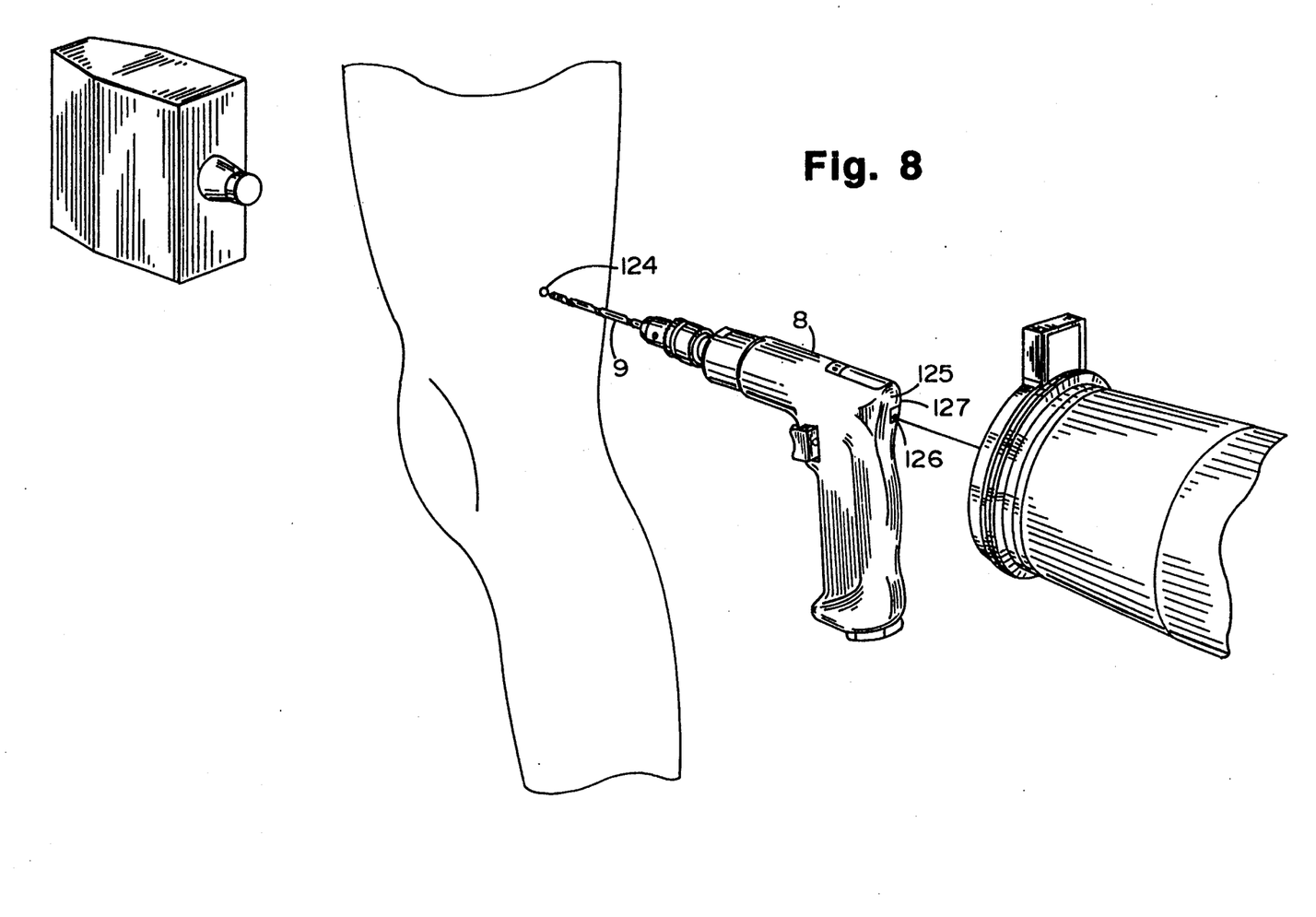
FIG. 8, is a perspective diagrammatic view of surgical drill being used in conjunction with a low power laser beam emitted from a laser targeting device, aligned to an x-ray beam, the laser beam being used to maintain alignment of the drill during drilling of a hole in a bone.

In FIG. 8, there is shown the next stage, during which the point 124, of drill bit 9, is placed on the mark or incision made at the positon of laser light spot 121. Taking care to keep point 124, of drill bit 9, on the position of laser light spot 121, the back 125, of drill 8, is manipulated into the laser beam until laser light spot 126, is brought onto the drill axis point marked at 127.

Many models of orthopaedic drill have a rear main bearing cap or marked target 127, which neatly indicates the correct axial position when the laser light spot appears on it. If there is no bearing cap or target at the rear of the drill, the axial position should be determined and permanently marked on the drill before any procedure relying upon laser targeting device 10, is commenced.

Figure 9:
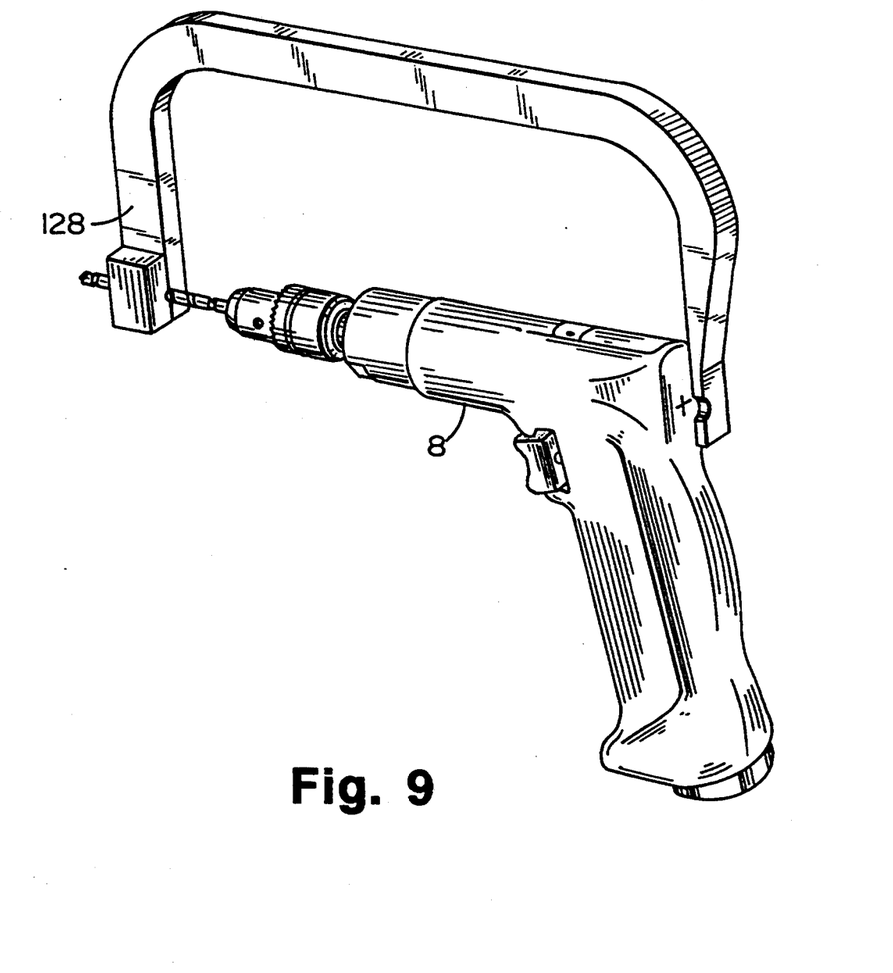
FIG. 9, is a perspective view of a surgical drill in a jig used for marking the point where the drill axis emerges from the rear of the drill case.

In FIG. 9, there is shown a surgical drill fitted to a jig 128. Jig 128, is designed to allow marking of the rear axis point of any drill that is provided with the well known Jacob's chuck or any other chuck which can axially mount a standard drill bit or rod. Since surgical drills must be sterile it is essential that the drill axis is marked permanently before sterilisation is carried out. The design of the jig allows marking to be done easily with a sharp instrument. One convenient way that we have established with the jig is to use another drill and suitably sized bit, starting the second drill and lightly touching the bit point to the axial point indicated by the jig on the back of the first drill.

We have not encountered any difficulty in seeing the red laser light spot in the presence of blood or incised tissue.

The image intensifier must be covered with sterile drapes to preserve the integrity of the sterile field and it will be apparent that the entire laser targeting device must also be covered. It is essential that this is accomplished in such a way as to allow the laser beam to exit from the drape with no significant degradation or loss of definition. A novel drape system forms an important part of the instant invention and ensures that basic requirements for commercialisation of the laser targeting device can be met.

Figure 10A:
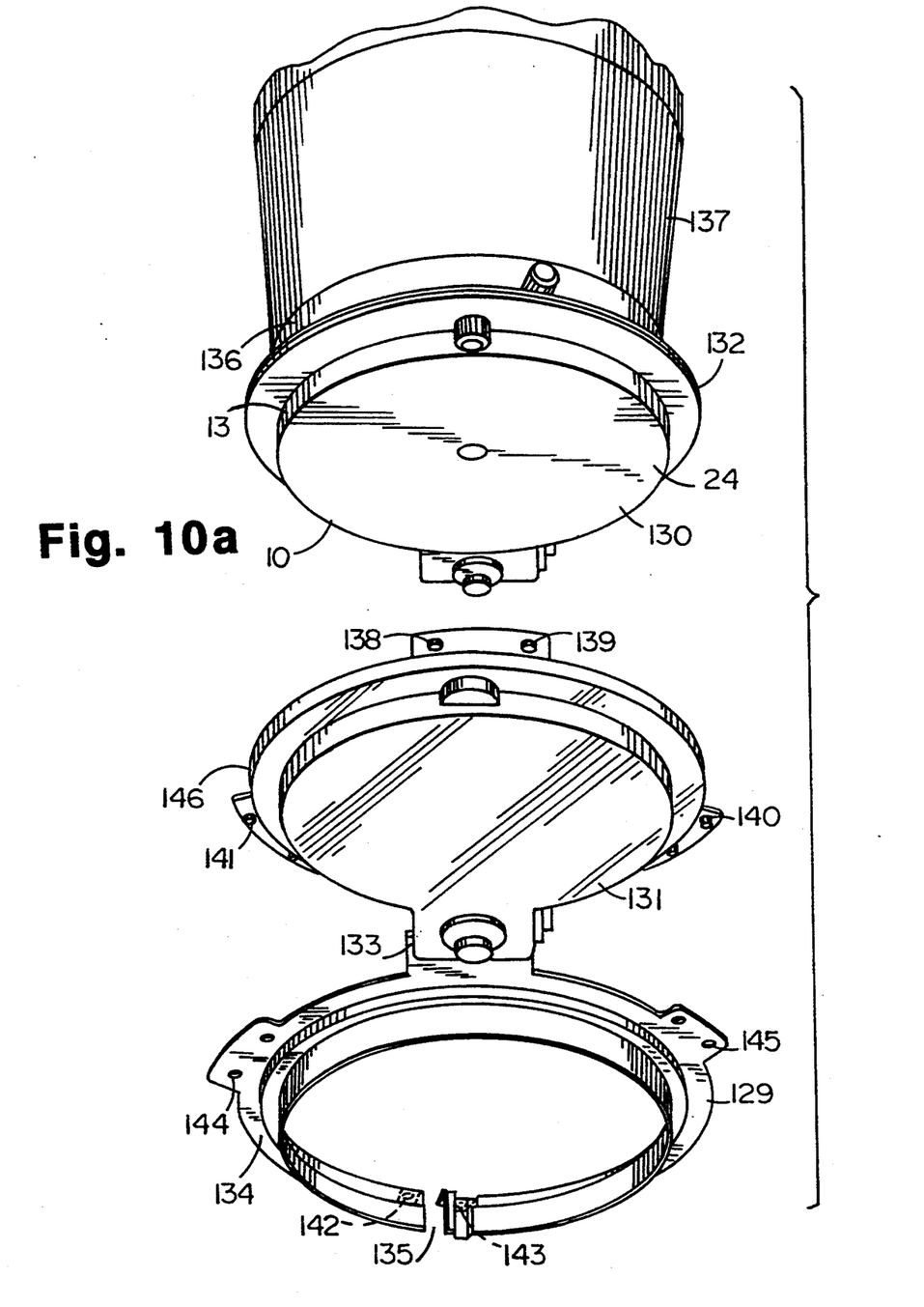
FIG. 10a and 10b, are perspective views in the open and closed positions, respectively, of a transparent semi-rigid drape according to the present invention, for covering a laser targeting device.

Turning now to FIG. 10a, there is shown part of a drape system for use in conjunction with an image intensifier fitted with a laser targeting device according to the present invention. A drape 129, for a laser targeting device 10, is transparent and semi-rigid and is conveniently formed in clear plastics, for instance by a method such as vacuum forming. It is shown in the position of presentation to the underside 130, of laser targeting device 10.

Transparent semi-rigid drape 129, is so shaped that its lower portion 131, will fit intimately and flush to the floor 24, of case 13 and closely around the rim 132, of upper plate 14. Transparent semi-rigid drape 129, may then be folded over along a hinging zone, indicated at 133, to form an upper portion 134. Upper portion 134, is interrupted at the opposite end to hinging zone 133, at 135, so that it may be fitted around the upper components 136, of laser targeting device 10 and closely around lower part 137, of image intensifier target head 6. Transparent semi-rigid drape 129, is adapted so that upper portion 134, may be closed over and secured to, lower portion 131, conveniently, for instance, by the provision of indented capture points at 138–141 and nipples at 142–145. Upper portion 134, is further shaped such that when in the closed position, it overlaps around the edge 146, of lower portion 131.

Figure 10B:
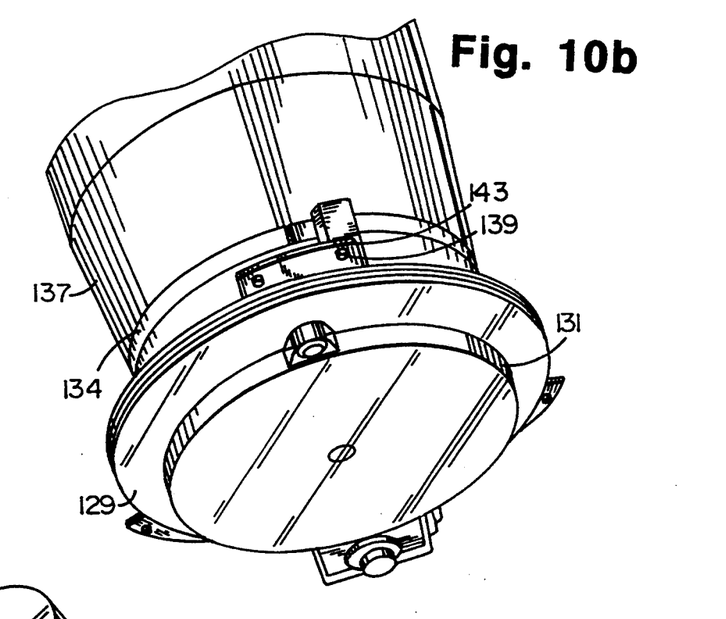

Transparent semi-rigid drape 129, is shown in the attached or closed position in FIG. 10b. It is to be clearly understood that transparent semi-rigid drape 129, though variable in shape and size, is distinguished from drapes of the prior art by having a lower portion, the shape of which is determined by the shape of the lower part of a laser targeting device according to the present invention and an upper part hinged to the lower part and which is substantially a flanged ring, the two parts being adapted to be secured together over a laser targeting device and around part of an image intensifier target head in such a way that the top overlaps the bottom.

Figure 11:
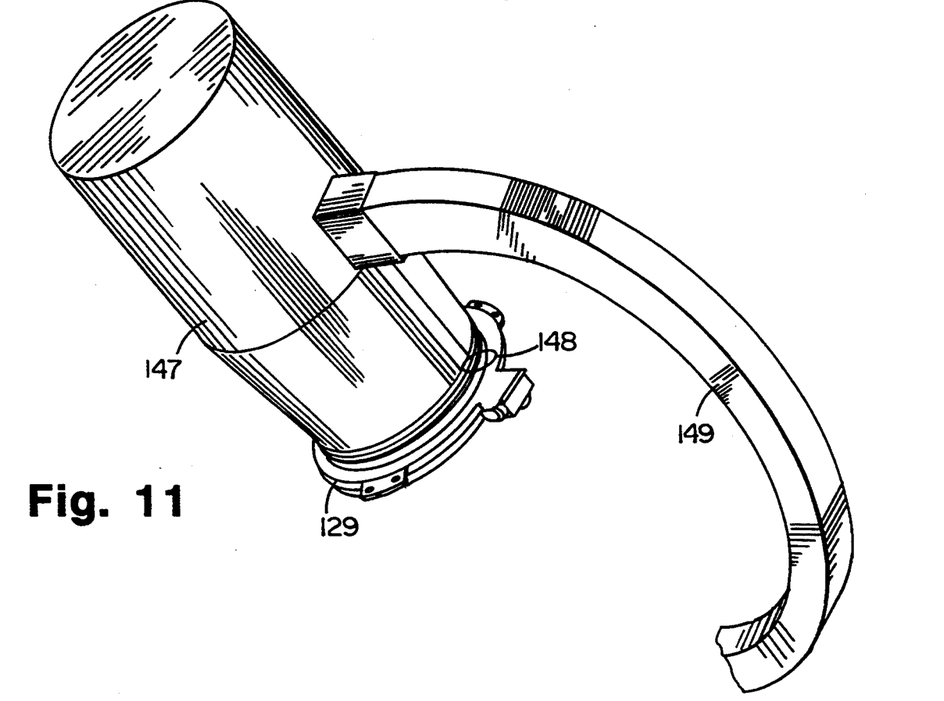
FIG. 11, is a diagrammatic view of a generally cylindrical drape, according to the present invention, in position on the target head of an image intensifier and being used in conjunction with a transparent semi-rigid drape.

In FIG. 11, there is shown, in position, a substantially cylindrical drape 147, for coveting the target head of an image intensifier. Cylindrical drape 147, may be conveniently formed in plastics, non woven or woven materials and is distinguished by being generally adapted to fit in a semi-tailored fashion to an image intensifier target head and specifically to close intimately over and around that part of transparent semi-rigid drape 129, which extends over the lower part of the image intensifier target head by the provision near the lower border of elastic means, drawstring means or adhesive taping means exemplified at 148. Cylindrical drape 147, must be closed off around the attachment between the 'C'-arm itself 149 and the target head (covered), preferably by taping. Drapes 129 and 147, are sterilised by any conventional method.

The remainder of the image intensifier system, the operating table and the patient may be draped by standard means but care must be taken not to interpose drape materials or any other artefact in the laser beam path.

Risks Involved in Using a Laser Source

The backs of many orthopaedic drills are treated so as to be non-reflecting and we recommend that if this was not done during manufacture, the drill should be so treated before use with the laser targeting device. However, the laser light source we prefer is of extremely low power and is of the same intensity as the kind used in teaching pointers. This ensures that the risk of retinal damage is very low indeed. There is no danger to the surgeon's hands and arms from exposure to the laser beam even if this was to be prolonged for any reason.

OTHER EMBODIMENTS AND APPLICATIONS

In the foregoing, we have described the most preferred embodiment, in which laser source 50, is positioned in such a way that the narrow beam that it produces travels radially into case 13. This is a substantial improvement over earlier preferred and fully functional embodiments where means for directing the laser and moving the mirror mount were actually in the beam path. That arrangement led to significant degradation of the image which was not acceptable in osteoporotic patients.

We contemplate and have made, other embodiments wherein the laser beam guiding arrangement has been substantially similar but the frame and mountings have been varied to fit non-standard machines or to fit at the source cone end of an image intensifier rather than at the target head end. All laser directing components have been similar but clamping ring 20 and its accessories have necessarily had to be different.

We contemplate and have used the laser targeting device in other applications apart from intramedullary nailing, including location and removal of penetrating foreign bodies such as a needle lodged in the calcaneum, shrapnel and bullets. It is very useful in pinpointing the position of screw heads in bone plates, especially when these are attached to the lower tibia since the screws can be removed under local rather than general anaesthesia in some cases. We further contemplate and are developing the use of the laser targeting device, according to the instant invention, in a wide variety of surgical applications outside orthopaedics including urology, ophthalmology, general surgery, neurosurgery, gynaecology, traumatology and veterinary practice, indeed wherever a reliable external reference point to an internal radio-opaque artefact would assist a surgeon, technician or other health care professional in caring for a patient.

We contemplate but have not yet made, an embodiment of the present invention where all the essential elements (or their structural equivalents) are integrated with an image intensifier, for instance, within the casing of the target head or within the casing of the source cone. We have further contemplated the advantages of providing integrated examples of the present invention within both the target head and the source cone. Once provided with the principles disclosed herein, these embodiments would be simple to construct, for those skilled in the art, without in any way departing from them.

Apart from health care applications we have conducted experiments, successful but so far limited, in non-health care applications of the laser targeting device in conjunction with image intensifiers, such as the location of failure sites in fatigued radio-opaque components housed within a relatively radiolucent matrix.

Fitting the laser targeting device to non-standard image intensifiers and making versions to fit the fairly recently introduced mini machines can be accommodated readily within the scope of the present invention and indeed it will be evident to those skilled in the art that many other embodiments can be made without departing from the principles disclosed herein.

Therefore, what we claim is:

1. A laser targeting device for use during surgical procedures and adapted for attachment to an x-ray image intensifier comprising:
   a. a laser light source and laser beam directing means for a laser beam emanating therefrom adapted to permit continuously variable reciprocating motion in the x-y plane about the z axis and in the x-z plane about the y axis but substantially excluding motion in the y-z plane about the x axis, said directing means being additionally adapted to provide mounting means for said laser light source;
   b. a housing for said laser light source and said directing means adapted by the provision of mounting means such that said housing is always outside that part of the path of an x-ray beam produced by an x-ray source cone and which impinges upon the working area of the target head or receiver of said image intensifier;
   c. a case characterized by upper and lower bounding surfaces disposed in a substantially flat and parallel manner and spaced apart by a wall suitably adapted by the provision of a hole constituting aperture means and receival means suitably disposed about said aperture means for the attachment of said mounting means of said housing, said aperture means being so sized as to permit the entry of said laser beam to the interior of said case which is adapted by the provision of adjustable mounting means which cooperate with clamping means for attachment of said laser targeting device to said target head such that said flat upper bounding surface is permitted to lie substantially flush against said target head of said image intensifier, said case being further adapted by the provision of a further hole located substantially centrally in said lower bounding surface and which is adapted to receive;

d. a plain substantially parallel sided transparent window to fit accurately said hole in said lower bounding surface said window constituting part of an assembly providing mounting means for a reflecting mirror disposed at an angle of 45 degrees to the plane in which said lower bounding surface of said case lies and also at 45 degrees to said x axis of said directing means such that when said laser beam is directed along said x-axis, through said aperture means into said case said mirror redirects said laser beam through said window along a path normal to it, said assembly being constructed from a small mass of thin walled substantially radiolucent materials and adapted to receive within that part of it which lies directly behind said mirror, a target; said adjustable mounting means of said case permitting limited variation in the disposition of the axis normal to the centre of said window about an axis normal to the geometric centre of said target head of said image intensifier, that part of said upper and said lower bounding members of said case which overlie the working area of said target head being substantially radiolucent;

e. substantially radio-opaque target means so positioned behind said mirror within said assembly that a ray path normal to the window, if extended backwards through said mirror would pass centrally through said target means; and f. separate calibrating means in the form of a radio-opaque marker within a suitable housing and marking guide such that when said calibration means is applied to the source cone, the point of emanation of an x-ray beam therefrom may be determined and marked, Said means being adapted to co-operate together such that said laser beam may be rendered substantially co-axial with said x-ray beam directed towards said target head to which said laser targeting device is attached such that the path of said x-ray beam may be illuminated at its point of impingement upon an object interposed between said source cone and said target of said x-ray beam and further providing a visible reference point corresponding to the effective centre of said x-ray beam on a monitor screen with said x-ray image intensifier.

2. A laser targeting device according to claim 1, wherein laser beam directing means are in the form of a. a turntable adapted by the provision of a slot radial to its centre of rotation, the axis of which is about the z axis and located at a suitable distance from said centre of rotation, said slot being further adapted to be engaged slidingly and intimately by a circular cam mounted eccentrically upon a shaft which is at right angles to the base of said turntable said shaft extending through to the outside of and secured to a first side of said housing which is adapted to receive it, said shaft terminating in a drive wheel by means of which said shaft may be rotated causing said turntable make angular excursions in the x-y plane about a central position, such excursions being defined by the relative dimensions of said slot, said eccentric cam and said shaft and the mounting position of said eccentric cam upon said shaft, said turntable being further adapted to receive, by the provision of mounting means in the form of bearings to permit motion at right angles to the plane of motion of said turntable of b. a laser mount adapted by the provision of journals and including an extended portion wherein is provided a slot radial to its centre of rotation, which is about the y axis and located at a suitable distance from said centre of rotation, said slot being further adapted to be engaged slidingly and intimately by a circular cam mounted eccentrically upon a shaft which is at right angles to the base of said laser mount said shaft extending through to the outside of and secured to a second side of said housing which is adapted to receive it, said shaft terminating in a drive wheel by means of which said shaft may be rotated causing said laser mount to make angular excursions in the x-z plane about a central position, such excursions being defined by the relative dimensions of said slot, said eccentric cam and said shaft and the mounting position of said eccentric cam upon said shaft.

3. A laser targeting device according to claim 1, wherein substantially radio-opaque target means comprise an arrangement of first and second arms which are substantially co-linear and of equal length and are disposed substantially at right angles to third and fourth arms which are also substantially co-linear and of equal length, the combined lengths of said first and second arms is less than the combined length of said third and fourth arms, said arrangement being disposed behind said mirror in a substantially co-planar and contiguous manner with said mirror such that said third and fourth arms lie in the x-z plane such that the image produced on said image intensifier monitor screen represents all four arms as apparently having equal length.

4. A laser targeting device according to claim 1, wherein separate calibrating means comprises a flanged discoid moulding divided into four symmetrical recessed areas by incomplete radial slots so sized as to accommodate the nib of a typical permanent marking pen and provided with a small radio opaque spheroid at its centre.

5. A laser targeting device according to claim 1, wherein is provided a transparent semi-rigid drape, adapted so that its lower portion fits over and flush against said lower bounding surface of said case extending to the rim of said upper bounding surface, said drape is further adapted by the provision of a hinge zone which defines an overfolded upper portion substantially in the form of a flanged ring which is rendered non-entire by an interruption at the opposite side from of said hinging zone by means of which said flanged ring may be fired around said clamping means and closely around the lower part of said target head, such that said flanged ring may overlap and be secured to said lower portion of said drape over said laser targeting device and said lower part of said target head.

6. A laser targeting device according to claims 1 or 5, wherein is provided a substantially cylindrical drape generally adapted to fit in a semi-tailored fashion over said target head and specifically to close intimately over and around the upper portion of said flanged ring of said transparent semi-rigid drape which extends over the lower part of said target head by the provision near the lower border of securing means.

* * * * *